US00PP34003P2

(12) United States Plant Patent
O'Connell

(10) Patent No.: US PP34,003 P2
(45) Date of Patent: Mar. 8, 2022

(54) ***ALOE* PLANT NAMED 'PHANTASM'**

(50) Latin Name: *Aloe ciliaris*
Varietal Denomination: PHANTASM

(71) Applicant: Altman Specialty Plants, Inc, Vista, CA (US)

(72) Inventor: Renee O'Connell, Escondido, CA (US)

(73) Assignee: Altman Specialty Plants Inc., Vista, CA (US)

( * ) Notice: Subject to any disclaimer, the term of this patent is extended or adjusted under 35 U.S.C. 154(b) by 0 days.

(21) Appl. No.: 17/357,586

(22) Filed: Jun. 24, 2021

(51) Int. Cl.
*A01H 5/00* (2018.01)

(52) U.S. Cl.
USPC ..... Plt./373

(58) Field of Classification Search
USPC ..... Plt./373
See application file for complete search history.

*Primary Examiner* — Annette H Para
(74) *Attorney, Agent, or Firm* — Cassandra Bright

(57) ABSTRACT

A new and distinct cultivar of *Aloe* plant named 'PHANTASM' is disclosed, characterized by vertical rosettes of variegated leaves, with an overall milky pale lemon green shading, pale yellow margins and tiny marginal teeth. Plants of the new variety grow with a more upswept morphology, thereby reducing the leaf breakage that is prevalent among many other *Aloes* with a more lateral morphology. *Aloe* 'Phantasm' is a relatively fast and robust grower, unusual for a variegate. The new variety is an *Aloe*, typically produced as a garden or container plant.

3 Drawing Sheets

Latin name of the genus and species: *Aloe ciliaris.*
Variety denomination: 'PHANTASM'.

BACKGROUND OF THE INVENTION

The new cultivar is a product of chance discovery. The new variety was discovered as a naturally occurring whole plant mutation of the parent variety. The parent is an unpatented, unnamed variety of *Aloe ciliaris*. Selection of the new variety was made in August of 2016 at a commercial greenhouse in Vista, Calif.

Asexual reproduction of the new cultivar 'PHANTASM' was first performed by vegetative cuttings at a commercial nursery in Vista, Calif. in October 2016. 'PHANTASM' has since produced several generations and has shown that the unique features of this cultivar are stable and reproduced true to type.

SUMMARY OF THE INVENTION

The cultivar 'PHANTASM' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'PHANTASM.' These characteristics in combination distinguish 'PHANTASM' as a new and distinct *Aloe* cultivar:

1. The new cultivar *Aloe* 'Phantasm' forms rosettes of leaves with overall milky pale lemon green shading, pale yellow margins and tiny marginal teeth. Center of leaves are overall milky lemon green, with unique emerald green striations.
2. *Aloe* 'Phantasm' grows with a more upswept morphology, thereby reducing the leaf breakage that is prevalent among many other *Aloes* with a more lateral morphology causing the leaves to extend over the edges of the pots. The more upright morphology is a benefit for the commercial nursery as shipment does not cause unsightly leaf breakage to the product.
3. *Aloe* 'Phantasm', with its milky color creates a novel purchase for the customer, and can be used in mixed plantings of colorful perennials or along with other colorful *Aloes* to provide an attractive accent.
4. *Aloe* 'Phantasm' is a relatively fast and robust grower, unusual for a variegate.

PARENTAL COMPARISON

*Aloe* 'Phantasm' differs from the parent *Aloe ciliaris* variety in that it is a variegate and exhibits coloration of milky pale yellow green, rather than the overall emerald green coloration of *Aloe ciliaris* hybrid.

COMMERCIAL COMPARISON

'PHANTASM' can be compared to the unpatented commercial variety *Aloe* 'Blue Elf'. The two *Aloe* varieties are similar in most horticultural characteristics; however, the new variety differs in the following:

1. *Aloe* 'Phantasm' produces ornate rosettes of rigid green leaves, liberally dappled with light yellow-green or greyed-green spots, whereas *Aloe* 'Blue Elf' exhibits taller rosettes of longer matte blue leaves with no spots.
2. *Aloe* 'Phantasm' fills an 8" pot with a single cut, whereas *Aloe* 'Blue Elf' fills an 8" pot only after a much longer interval with the production of offsets.
3. *Aloe* 'Phantasm' displays wide, strong leaves which are contained within the perimeter of the pot, whereas *Aloe* 'Blue Elf' produces softer, longer leaves which can break in shipping.
4. *Aloe* 'Phantasm' forms thick, rigid leaves that do not "blanch" or exhibit "tip death", whereas those of *Aloe* 'Blue Elf' are thinner and are known to suffer "blanch" or "tip death" under certain circumstances in the commercial environment.

BRIEF DESCRIPTION OF THE PHOTOGRAPHS

The photographs were taken using conventional techniques and equipment. While the colors in these photographs may display variances of color as compared to the living cultivar, due to LRV (light reflectance value), they are as accurate as possible using conventional photographic techniques. Colors in the photographs may appear to differ slightly from the color values cited in the botanical description, which accurately describe the colors of the new cultivar *Aloe* 'Phantasm'.

DETAILED BOTANICAL DESCRIPTION

Figure 1:
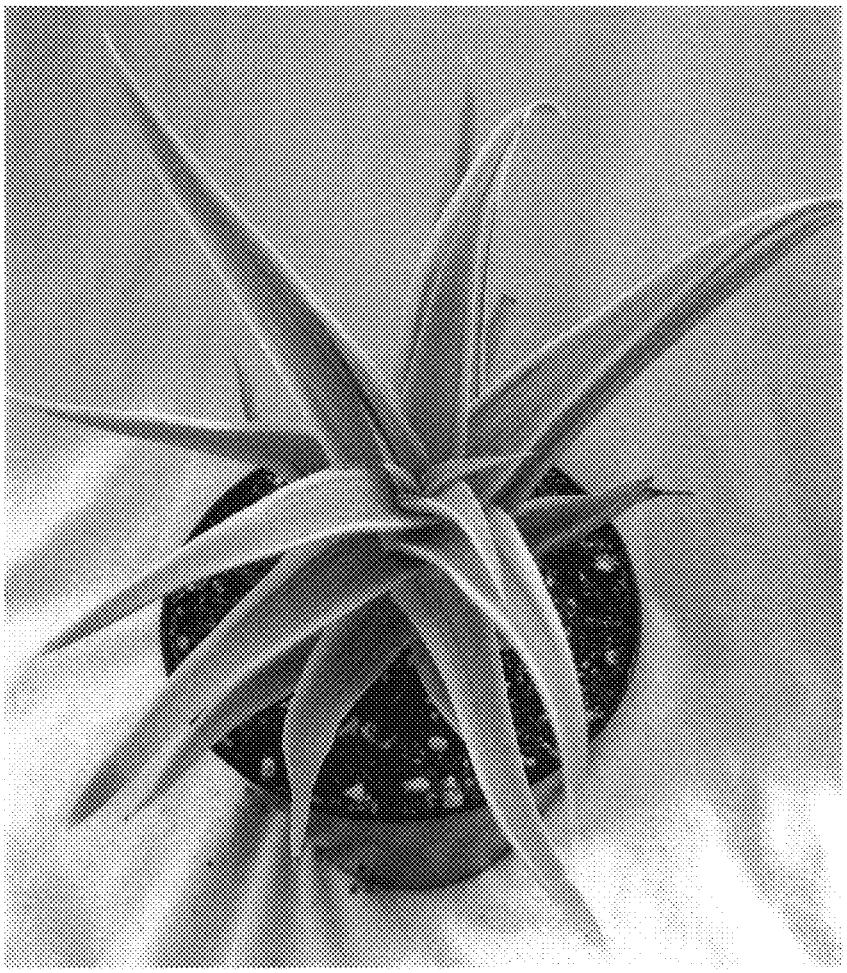
FIG. 1 illustrates in full color a plant with a single rosette of *Aloe* 'Phantasm', at about 5 months, grown in a greenhouse (approximately 2500 foot candles) in Vista, Calif.
Figure 2:
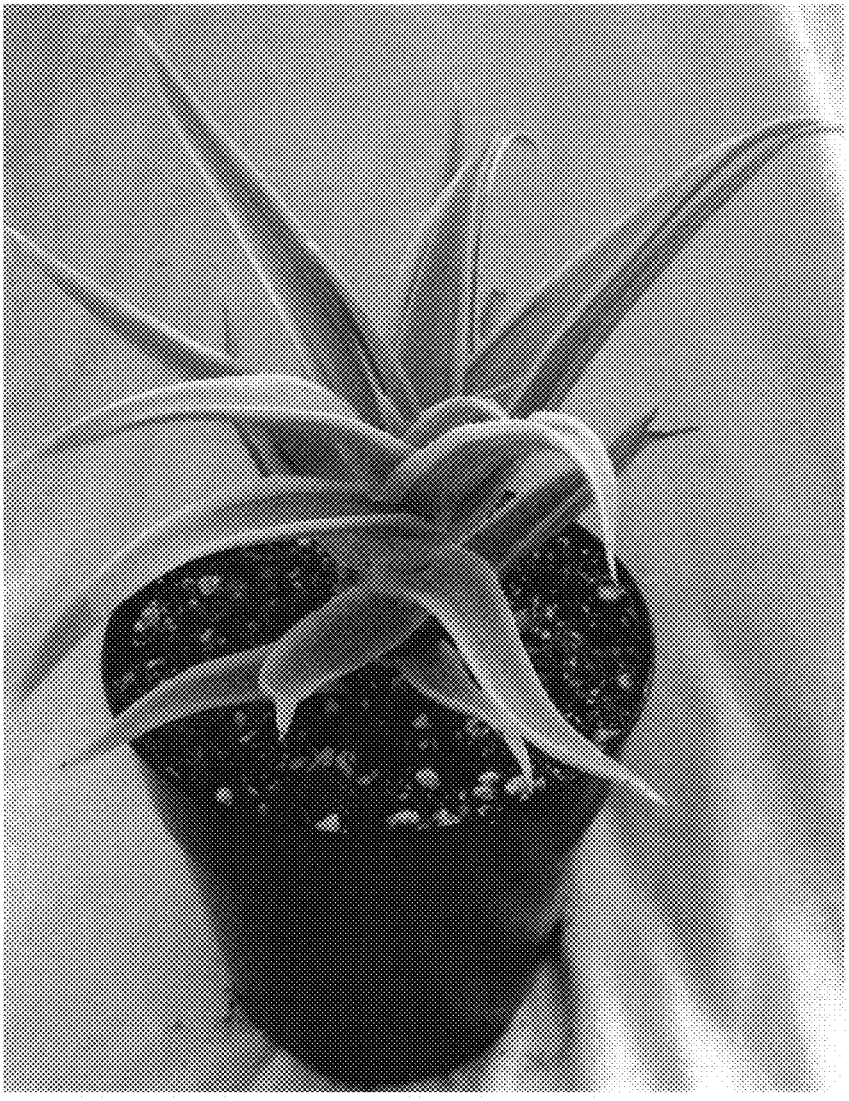
FIG. 2 illustrates in full color the rosette of FIG. 1 from a different angle.
Figure 3:
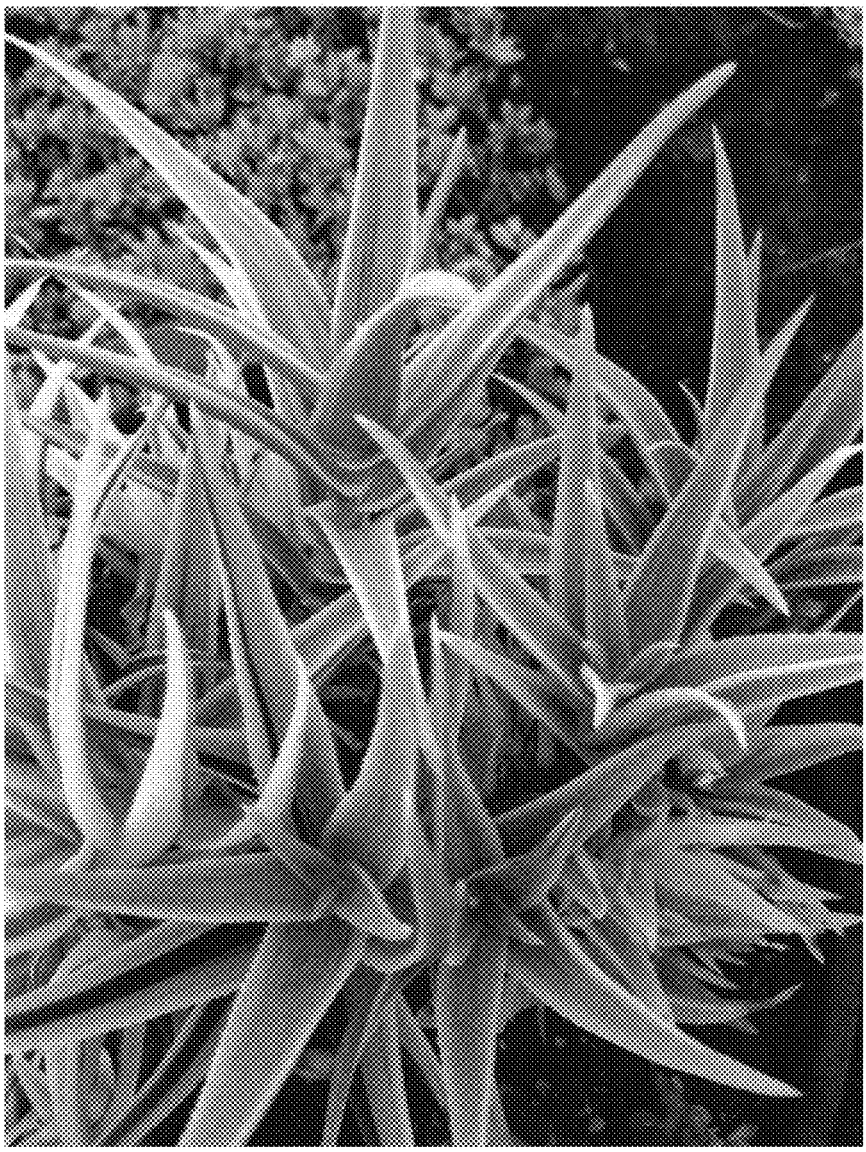
FIG. 3 illustrates in full color an older plant of *Aloe* 'Phantasm', closer to 1 year old, with offsets, grown in a greenhouse (approximately 2500 foot candles) in Vista, Calif.

In the following description, color references are made to The Royal Horticultural Society Color Chart, 2007 edition, except where general terms of ordinary dictionary significance are used. The following observations and measurements describe 'PHANTASM' plants grown in a commercial nursery in Vista, Calif. Temperatures ranged from about −1° C. to 39° C. No artificial light, photoperiodic treatments or chemical treatments were given to the plants. Natural light conditions were approximately 2500 to 3000 fc of light. Measurements and numerical values represent averages of typical plant types.

Botanical classification: *Aloe ciliaris* 'PHANTASM'.

Age of the plant described: About 5 months.

PROPAGATION

Time to initiate roots: Approximately 25 days at 22° C.

Root description: Fibrous. Brown, not accurately measured with the RHS chart.

Propagation method: Vegetative cuttings.

PLANT

Growth habit: Upright succulent.

Container size: 5 inch.

Height: Approximately 17 cm.

Plant spread: Approximately 17 cm.

Growth rate: Moderate for *Aloe ciliaris*, rapid for a variegated *Aloe*.

Branching characteristics: No branches, rosette forming.

Central stem:

*Length.*—About 12 cm.

*Width.*—10 to 14 mm.

*Color.*—Near Green-White 157A.

*Texture.*—Glabrous.

*Appearance.*—Matte.

*Strength.*—Moderately strong.

*Internode.*—About 3 to 5 mm.

FOLIAGE

Leaf:

*Arrangement.*—Spiral.

*Average length.*—Average range 8 cm to 12 cm.

*Average width.*—2.2 cm.

*Average thickness.*—2 mm.

*Shape of blade.*—Very narrow deltoid.

*Apex.*—Acute.

*Base.*—Clasping.

*Margin.*—Small, slightly sharp dentations occurring at regular intervals of about 3 mm apart. Dentations about 1 to 2 mm tall.

*Aspect.*—Moderately reflexed.

*Angle of attachment.*—Upswept, acute angle.

*Texture of top surface.*—Smooth.

*Texture of bottom surface.*—Smooth.

*Quantity of leaves.*—Average 25.

*Color.*—Young foliage upper side: Near RHS Green 138D streaked Green 141C. Overall overlay shading near Yellow-Green 145D. Young foliage under side: Near RHS Green 138D streaked Green 141C. Overall overlay shading near Yellow-Green 145D. Mature foliage upper side: Near RHS Green 138D streaked Green 141A and 141C. Overall overlay shading near Yellow-Green 150D. Mature foliage under side: Near RHS Green 138D streaked Green 141A and 141C. Overall overlay shading near Yellow-Green 150D. Venation: Linear. Color: Indistinguishable from leaf blade.

FLOWER

Not observed to date.

REPRODUCTIVE ORGANS

Not observed to date.

OTHER CHARACTERISTICS

Seeds and fruits: Not observed to date.

Temperature tolerance: Tolerates temperatures from approximately −2° C. to at least 40° C.

Disease/pest resistance: Neither resistance nor susceptibility observed.

What is claimed is:

1. A new and distinct cultivar of *Aloe* plant named 'PHANTASM' as herein illustrated and described.

* * * * *